(12) United States Patent
Jeong et al.

(10) Patent No.: US 8,598,309 B2
(45) Date of Patent: Dec. 3, 2013

(54) CATALYTIC SYSTEM OF NITRATE ANIONS FOR CO₂/EPOXIDE COPOLYMERIZATION

(75) Inventors: Ji Su Jeong, Daejeon (KR); Sujith Sudevan, Daejeon (KR); Myung Ahn Ok, Daejeon (KR); Sung Jae Na, Daejeon (KR); Yong Gyu Han, Daejeon (KR); Kwang Jin Chung, Daejeon (KR); Bun Yeoul Lee, Suwon-si (KR); Kodiyan Varghese Jobi, Suwon-si (KR)

(73) Assignee: SK Innovation Co., Ltd., Seoul (KR)

( * ) Notice: Subject to any disclaimer, the term of this patent is extended or adjusted under 35 U.S.C. 154(b) by 199 days.

(21) Appl. No.: 13/033,252

(22) Filed: Feb. 23, 2011

(65) Prior Publication Data

US 2011/0207909 A1    Aug. 25, 2011

(30) Foreign Application Priority Data

Feb. 25, 2010  (KR) .................. 10-2010-0017049

(51) Int. Cl.
| | |
|---|---|
| C08G 59/68 | (2006.01) |
| C08G 65/10 | (2006.01) |
| C08G 65/12 | (2006.01) |
| C08G 65/04 | (2006.01) |
| C08F 4/06 | (2006.01) |
| C08F 4/22 | (2006.01) |

(52) U.S. Cl.
USPC ........ 528/412; 528/410; 528/482; 528/502 C; 528/502 R; 528/405; 528/409; 502/102; 502/103; 502/104; 502/201

(58) Field of Classification Search
USPC .................. 502/103, 104, 201, 102; 528/410, 528/502 C, 502 R, 405, 409, 412
See application file for complete search history.

(56) References Cited

FOREIGN PATENT DOCUMENTS

| | | |
|---|---|---|
| CN | 101020747 A | 8/2007 |
| KR | 100853358 B1 | 8/2008 |
| KR | 1020090090154 A | 8/2009 |
| WO | 2008136591 A1 | 11/2008 |

OTHER PUBLICATIONS

Lu et al; Bifunctional catalyst used for preparation of polycarbonate; Aug. 2007; Dalian University of Technology, Peop. Rep. China; Chem Abstract 147: 365929.*
Noh et al., "Two Components in a Molecule: Highly Efficient and Thermally Robust Catalytic System for CO2/Epoxide Copolymerization", J. Am. Chem. Soc., 2007, pp. 8082-8083, vol. 129.
Sujith et al., "A Highly Active and Recyclable Catalytic System for CO2/Propylene Oxide Copolymerization", Angew. Chem. Int. Ed., 2008, pp. 7306-7309, vol. 47.
Na et al., "Elucidation of the Structure of a Highly Active Catalytic System for CO2/Epoxide Copolymerization: A salen-Cobaltate Complex of an Unusual Binding Mode", Inorg. Chem., 2009, pp. 10455-10465, vol. 48, No. 21.
Min et al., "Efficient Synthesis of a Highly Active Catalyst for CO2/Epoxide Copolymerization", Bull. Korean Chem. Soc., 2009, pp. 745-748, vol. 30, No. 3.
Desai et al., "Production of Organic Intermediates", Phamaceutical and Dyestuff, Sarup & Sons, 2005, p. 5, New Delhi.

* cited by examiner

Primary Examiner — Duc Truong
(74) Attorney, Agent, or Firm — The Webb Law Firm

(57) ABSTRACT

This invention relates to a Salen type ligand including three or more quaternary ammonium salts of nitrate anions, to a trivalent metal complex compound prepared from this ligand and a method of preparing the same, to a method of preparing polycarbonate by copolymerizing an epoxide compound and carbon dioxide using the complex compound as a catalyst, and to a method of separating and collecting the catalyst from the copolymer after copolymerization. This catalyst used to copolymerize an epoxide compound and carbon dioxide can be more simply prepared, and has lower catalyst preparation and recovery costs, and higher activity, compared to conventional catalysts.

15 Claims, No Drawings

CATALYTIC SYSTEM OF NITRATE ANIONS FOR CO₂/EPOXIDE COPOLYMERIZATION

BACKGROUND OF THE INVENTION

1. Technical Field

The present invention relates to a Salen type ligand including three or more quaternary ammonium salts of nitrate anions, to a trivalent metal complex compound prepared from the ligand and a method of preparing the same, to a method of preparing polycarbonate by copolymerizing an epoxide compound and carbon dioxide using the complex compound as a catalyst, and to a method of separating and recovering the catalyst from the copolymer after copolymerization.

2. Description of the Related Art

Aliphatic polycarbonate is a polymer which is easily biodegradable, and is useful for example as a packaging material or a coating material. Preparation of polycarbonate from an epoxide compound and carbon dioxide is very environmentally friendly because phosgene which is poisonous is not used and carbon dioxide may be inexpensively obtained.

Many researchers have developed various types of catalysts in order to produce polycarbonate from an epoxide compound and carbon dioxide since 1960. The present inventors have recently disclosed a catalyst having high activity and high selectivity synthesized from a quaternary ammonium salt-containing Salen [H₂Salen=N,N'-bis(3,5-dialkylsalicylidene)-1,2-ethylenediamine] type ligand [Bun-Yeoul Lee, Korean Patent No. 10-0853358 (issue date: 2008.08.13); Bun-Yeoul Lee, Sujith S, Eun-Kyung Noh, Jae-Ki Min, Korean Patent Application No. 10-2008-0015454 (filing date: 2008.02.20); Bun-Yeoul Lee, Sujith S, Eun-Kyung Noh, Jae-Ki Min, PCT/KR2008/002453 (filing date: 2008.04.30); Eun-Kyung Noh, Sung-Jae Na, Sujith S, Sang-Wook Kim, and Bun-Yeoul Lee* *J. Am. Chem. Soc.* 2007, 129, 8082-8083 (2007.07.04); Sujith S, Jae-Ki Min, Jong-Eon Seong, Sung-Jae Na, and Bun-Yeoul Lee, *Angew. Chem. Int. Ed.*, 2008, 47, 7306-7309 (2008.09.08)]. The catalyst disclosed by the present inventors may be highly active and highly selective and enables the preparation of a copolymer having high molecular weight and polymerization to be carried out even at high temperature and thus may be applied to commercial processes. Furthermore, this catalyst is advantageous because a quaternary ammonium salt is contained in the ligand, and thus the catalyst may be easily separated from the copolymer after copolymerization of carbon dioxide and epoxide, and re-used.

Also, the present inventors have carefully examined a catalyst having higher activity and higher selectivity among the catalyst group of the above patent and thus have proved that such a catalyst has a peculiar structure in which a nitrogen atom of the Salen-ligand is not coordinated but only an oxygen atom is coordinated to a metal, which was not known to date (see Structure 1 below, Sung-Jae Na, Sujith S, Anish Cyriac, Bo-Eun Kim, Jina Yoo, Youn K. Kang, Su-Jung Han, Chongmok Lee, and Bun-Yeoul Lee* "Elucidation of the Structure of A Highly Active Catalytic System for CO₂/Epoxide Copolymerization: A Salen-Cobaltate Complex of An Unusual Binding Mode" *Inorg. Chem.* 2009, 48, 10455-10465).

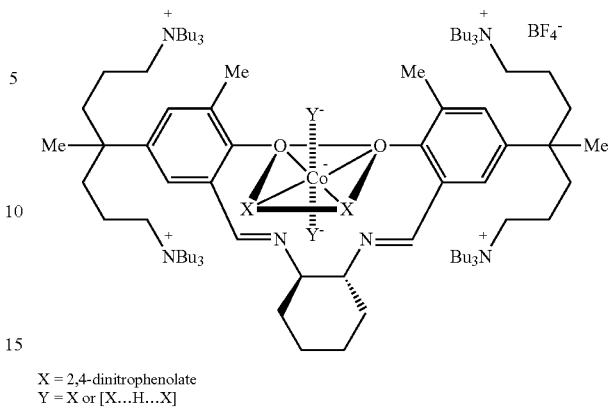

X = 2,4-dinitrophenolate
Y = X or [X...H...X]

Furthermore, a method of easily synthesizing the ligand of the above compound has been developed (Min, J.; Seong, J. E.; Na, S. J.; Cyriac, A.; Lee, B. Y. *Bull. Korean Chem. Soc.* 2009, 30, 745-748). However, when considering the application of the highly active catalyst of Structure 1 to a commercial process, the following problems exist.

1) 2,4-dinitrophenolate or 2,4-dinitrophenol contained in the catalyst of Structure 1 is known to be explosive. Particularly the above material is known to be more explosive under dry conditions (K. R. Desai, B. G. Naik, *Production of Organic Intermediates (Phamaceutical and Dyestuff)*, Sarup & Sons, New Delhi, 2005; p 5). The catalyst of Structure 1 should be prepared and stored under dry conditions. This catalyst is unsuitable for mass production and continuous use.

2) When carbon dioxide/epoxide copolymerization is carried out using the catalyst of Structure 1, a polymer chain grows from 2,4-dinitrophenolate or 2,4-dinitrophenol contained in the catalyst of Structure 1. Briefly, the 2,4-dinitrophenol group is mainly attached to the end of the polymer chain. Upon recovery of the catalyst, 2,4-dinitrophenolate and 2,4-dinitrophenol are not recovered. Attaching a 2,4-dinitrophenol group to an end of any polymer chain causes the price of resin to increase. Furthermore, the 2,4-dinitrophenolate anion is considerably yellow-colored, and thus the resin may be pale yellow-colored even after removal of the catalyst.

3) The preparation cost of the catalyst of Structure 1 is high. The synthesis method thereof is described below (*Bull. Korean Chem. Soc.* 2009, 30, 745-748). This method is inappropriate for mass production because of the following problems.

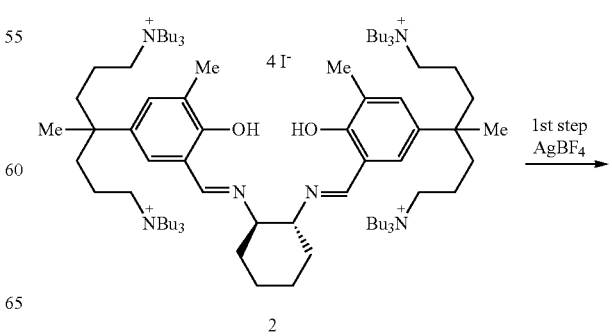

2

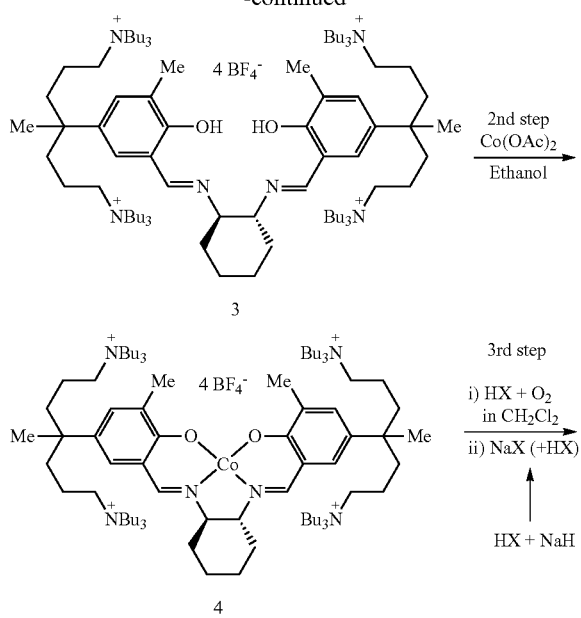

i) AgBF₄ used in the first step is very expensive and thus mainly results in high catalyst preparation cost, and also mass production or purchasing thereof is not easy.

ii) The second step should be performed in an atmosphere without oxygen. Specifically, oxygen must be thoroughly removed from ethanol which is a solvent, but it is not easy to completely remove oxygen from ethanol.

iii) Sodium 2,4-dinitrophenolate used in the third step should be used in a dry state. In order to prepare dry sodium 2,4-dinitrophenolate, NaH and anhydrous THF solvent should be used. However, NaH is high-priced and has high ignitability and is thus difficult to mass handle. Furthermore, removing moisture from the THF solvent is a large burden in terms of mass production.

4) NaBF₄ is used when recovering the catalyst of Structure 1, but is expensive, thus negating economic benefits.

Also analogous compounds having nitrate anions are disclosed in Chinese Patent (CN 100494248C (2009.06.03)), in which only compounds having a total of two quaternary ammonium salts to $R^5$ and $R^6$ and having four ammonium salts to $R^1$, $R^2$, $R^5$ and $R^6$ are described, which falls out of the range of a complex compound according to the present invention.

SUMMARY OF THE INVENTION

Accordingly, the present inventors have studied to solve the problems encountered in the related art and thus found the fact that nitrate and acetate anions may be introduced in place of 2,4-dinitrophenolate, thereby solving the problems of 1) and 2) of the catalyst of Structure 1. Furthermore, when synthesizing a catalyst having introduced nitrate and acetate anions, not AgBF₄ but AgNO₃ or Ag(OAc) may be used, thus considerably reducing the preparation cost, enabling mass production and purchasing, obviating the need to use ethanol without oxygen, and not using sodium 2,4-dinitrophenolate to thus eliminate the need for NaH and anhydrous THF, thereby solving the problems of 3) of the catalyst of Structure 1. Furthermore, nitric acid or nitrate salt which is comparatively inexpensive may be used instead of NaBF₄ which is a non-reactive salt conventionally used upon recovery of the catalyst, and thus the problems of 4) of the catalyst of Structure 1 may be solved.

Therefore, a first object of the present invention is to provide a Salen type ligand including three or more quaternary ammonium salts of nitrate anions, a trivalent metal complex compound prepared from this ligand, and a method of preparing the same.

A second object of the present invention is to provide a method of preparing polycarbonate by copolymerizing an epoxide compound and carbon dioxide using the complex compound as a catalyst.

A third object of the present invention is to provide a method of separating and recovering the catalyst from a mixture solution of catalyst and copolymer, after production of the copolymer using the complex compound as a catalyst.

DESCRIPTION OF SPECIFIC EMBODIMENTS

Hereinafter, embodiments of the present invention will be described in detail.

The present invention provides a compound represented by Formula 1 below.

[Formula 1]

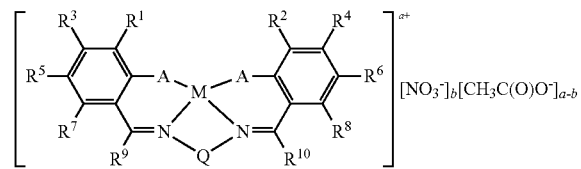

In Formula 1, M is trivalent cobalt or trivalent chromium;
A is an oxygen or sulfur atom;
Q is a diradical that connects two nitrogen atoms;
$R^1$ and $R^2$ are each independently (C1-C20) primary alkyl;
$R^3$ to $R^{10}$ are each independently hydrogen; halogen; (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; (C1-C20)alkoxy; (C6-C30)aryloxy; formyl; (C1-C20)alkylcarbonyl; (C6-C20)arylcarbonyl; or a metalloid radical of Group 14 metal substituted with hydrocarbyl;
two of $R^1$ to $R^{10}$ may be linked with each other to form a ring;
at least three of $R^3$ to $R^{10}$ are a proton group selected from among Formula a, Formula b and Formula c as represented below:

[Formula a]

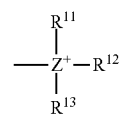

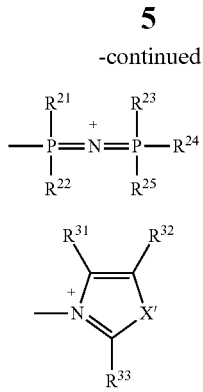

[Formula b]

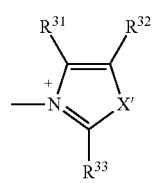

[Formula c]

Z is nitrogen or phosphorus;

$R^{11}$, $R^{12}$, $R^{13}$, $R^{21}$, $R^{22}$, $R^{23}$, $R^{24}$ and $R^{25}$ are each independently (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; or a metalloid radical of Group 14 metal substituted with hydrocarbyl; two of $R^{11}$, $R^{12}$ and $R^{13}$ or two of $R^{21}$, $R^{22}$, $R^{23}$, $R^{24}$ and $R^{25}$ may be linked with each other to form a ring;

$R^{31}$, $R^{32}$ and $R^{33}$ are each independently hydrogen; (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; or a metalloid radical of Group 14 metal substituted with hydrocarbyl; two of $R^{31}$, $R^{32}$ and $R^{33}$ may be linked with each other to form a ring;

X' is oxygen, sulfur or N—R (wherein R is (C1-C20)alkyl);

a is a number obtained by adding 1 to the number of proton groups included in $R^3$ to $R^{10}$;

b is an integer of 1 or more; and a nitrate or acetate anion may be coordinated to M.

The present invention provides a compound essentially including nitrate anions and partially including acetate anions. Korean Patent No. 10-0853358 (issue date: 2008.08.13) disclosed by the present inventors claims no nitrate anion and confines, as anions, halogen atom, nitro substituted or unsubstituted C1-C20 aryloxy, or halogen substituted or unsubstituted C1-C20 carboxyl anion, which differs from the present invention. The present invention is advantageous because nitrate and acetate anions are introduced instead of 2,4-dinitrophenolate and thus there is no explosiveness, and also because the nitrate or acetate group is attached to the end of the polymer chain, thus reducing the catalyst cost upon mass production.

The catalyst of Structure 1 in the related art has an octahedral structure in which nitrogen is not coordinated and the quaternary ammonium salt anion is coordinated so that cobalt has a negative formal charge, and is thus highly active (Inorg. Chem. 2009, 48, 10455-10465).

Because the nitrate anion which is a feature of the present invention has poor coordination performance, it is not strongly coordinated to cobalt, making it difficult to form a structure in which nitrogen is not coordinated and the quaternary ammonium salt anion is coordinated, as in the catalyst of Structure 1. However, when polymerization is initiated, the nitrate anion reacts with a monomer, thus forming a carbonate anion or alkoxy anion. The carbonate anion or alkoxy anion has high coordination performance, and may thus form a structure in which nitrogen is not coordinated and the quaternary ammonium salt anion is coordinated, as in the catalyst of Structure 1. In order to form the structure as in the catalyst of Structure 1, which shows high activity after initiation of the polymerization, the number of onium salts should be three or more, and primary alkyl in which steric hindrance of $R^1$ and $R^2$ is not large should be used. In the case where $R^1$ and $R^2$ are tertiary alkyl or secondary alkyl, the structure as in the catalyst of Structure 1 is not formed, resulting in low polymerization activity. Even when the number of onium salts is two or less, the structure as in the catalyst of Structure 1 is not formed, resulting in low polymerization activity (Inorg. Chem. 2009, 48, 10455-10465).

Preferably in Formula 1, M is trivalent cobalt; A is oxygen; Q is (C6-C30)arylene, (C1-C20)alkylene, (C2-C20)alkenylene, (C2-C20)alkynylene or (C3-C20)cycloalkylene, and more preferably Q is trans-1,2-cyclohexylene, phenylene or ethylene; $R^1$ and $R^2$ are each independently methyl or ethyl; $R^3$ to $R^{10}$ are each independently hydrogen or —[$YR^{41}_{3-m}\{(CR^{42}R^{43})_n N^+ R^{44}R^{45}R^{46}\}_m$] in which Y is C or Si; $R^{41}$, $R^{42}$, $R^{43}$, $R^{44}$, $R^{45}$ and $R^{46}$ are each independently hydrogen; (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; or a metalloid radical of Group 14 metal substituted with hydrocarbyl, two of $R^{44}$, $R^{45}$ and $R^{46}$ being linked with each other to form a ring; m is an integer from 1 to 3, and n is an integer from 1 to 20, in which at least three of $R^3$ to $R^{10}$ are —[$YR^{41}_{3-m}\{(CR^{42}R^{43})_n N^+ R^{44}R^{45}R^{46}\}_m$] when m is 1, at least two of $R^3$ to $R^{10}$ are —[$YR^{41}_{3-m}\{(CR^{42}R^{43})_n N^+ R^{44}R^{45}R^{46}\}_m$] when m is 2, or one or more of $R^3$ to $R^{10}$ are —[$YR^{41}_{3-m}\{(CR^{42}R^{43})_n N^+ R^{44}R^{45}R^{46}\}_m$] when m is 3.

More preferably, the complex compound of Formula 1 may be a complex compound of Formula 2 below.

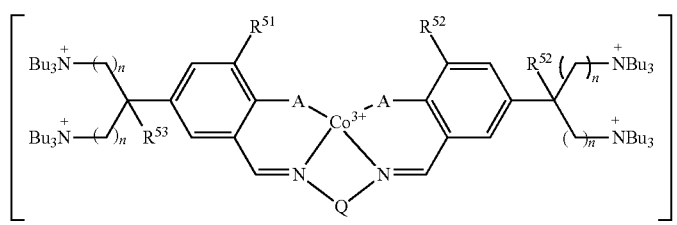

[Formula 2]

$[NO_3^-]_4[CH_3C(O)O^-]$.

In Formula 2, $R^{51}$ and $R^{52}$ are each independently methyl or ethyl;

$R^{53}$ and $R^{54}$ are each independently hydrogen or methyl;

Q is trans-1,2-cyclohexylene, phenylene or ethylene;

n is an integer from 1 to 20; and a nitrate anion and an acetate anion may be coordinated to cobalt.

Further preferably in Formula 2, $R^{51}$, $R^{52}$, $R^{53}$ and $R^{54}$ are methyl, n is 3, and Q is trans-1,2-cyclohexylene.

In addition, the present invention provides a method of preparing polycarbonate, including copolymerizing an epoxide compound and carbon dioxide using the complex compound of Formula 1 as a catalyst.

The epoxide compound is one or more selected from the group consisting of (C2-C20)alkylene oxide substituted or unsubstituted with halogen, (C1-C20)alkyloxy, (C6-C20) aryloxy or (C6-C20)ar(C1-C20)alkyloxy; (C4-C20)cycloalkylene oxide substituted or unsubstituted with halogen, (C1-C20)alkyloxy, (C6-C20)aryloxy or (C6-C20)ar(C1-C20)alkyloxy; and (C8-C20)styrene oxide substituted or unsubstituted with halogen, (C1-C20)alkyloxy, (C6-C20) aryloxy, (C6-C20)ar(C1-C20)alkyloxy or (C1-C20)alkyl. Examples of the aryloxy may include phenoxy, biphenyloxy, naphthyloxy, etc. The alkyloxy, aryloxy, aralkyloxy and alkyl may be those having a substituent selected from among halogen and alkoxy.

Specific examples of the epoxide compound include ethylene oxide, propylene oxide, butene oxide, pentene oxide, hexene oxide, octene oxide, decene oxide, dodecene oxide, tetradecene oxide, hexadecene oxide, octadecene oxide, butadiene monoxide, 1,2-epoxide-7-octene, epifluorohydrin, epichlorohydrin, epibromohydrin, isopropyl glycidyl ether, butyl glycidyl ether, t-butyl glycidyl ether, 2-ethylhexyl glycidyl ether, allyl glycidyl ether, cyclopentene oxide, cyclohexene oxide, cyclooctene oxide, cyclododecene oxide, alpha-pinene oxide, 2,3-epoxidenorbornene, limonene oxide, dieldrin, 2,3-epoxidepropylbenzene, styrene oxide, phenylpropylene oxide, stilbene oxide, chlorostilbene oxide, dichlorostilbene oxide, 1,2-epoxy-3-phenoxypropane, benzyloxymethyl oxirane, glycidyl-methylphenyl ether, chlorophenyl-2,3-epoxidepropyl ether, epoxypropyl methoxy phenyl ether, biphenyl glycidyl ether, and glycidyl naphthyl ether.

The epoxide compound may be used in polymerization using an organic solvent as a reaction medium, and examples of the solvent include aliphatic hydrocarbons such as pentane, octane, decane and cyclohexane, aromatic hydrocarbons such as benzene, toluene and xylene, and halogenated hydrocarbons such as chloromethane, methylene chloride, chloroform, carbon tetrachloride, 1,1-dichloroethane, 1,2-dichloroethane, ethyl chloride, trichloroethane, 1-chloropropane, 2-chloropropane, 1-chlorobutane, 2-chlorobutane, 1-chloro-2-methylpropane, chlorobenzene and bromobenzene, which may be used alone or in combinations of two or more thereof.

More preferably, bulk polymerization using a monomer itself as a solvent may be performed.

The molar ratio of epoxide to catalyst may range from 1,000 to 1,000,000, preferably from 50,000 to 200,000. As such, the conversion rate of the catalyst, namely the number of mols of epoxide consumed relative to 1 mol cobalt per time may be 500 or more turnover/hr. Upon copolymerization, the pressure of carbon dioxide may range from atmospheric pressure up to 100 atm, preferably from 5 atm to 30 atm, and also, the polymerization temperature may range from 20° C. to 120° C., preferably from 50° C. to 90° C.

The polycarbonate may be polymerized using batch polymerization, semi-batch polymerization, or continuous polymerization. When batch or semi-batch polymerization is used, the reaction time may be set to the range of 1-24 hours, preferably 1.5-4 hours. On the other hand, when using continuous polymerization, an average residence time of the catalyst may also be set to the range of 1.5-4 hours.

According to the present invention, polycarbonate having a number average molecular weight ($M_n$) ranging from 5,000 to 1,000,000 with a molecular weight distribution ($M_w/M_n$,) of 1.05~4.0 may be prepared. As such, $M_n$ indicates a number average molecular weight determined by using polystyrene having a single molecular weight distribution as a standard and then measuring its molecular weight by GPC, and $M_w/M_n$, is a ratio of weight average molecular weight and number average molecular weight specified by GPC using the same process.

The prepared polycarbonate polymer is composed of 80% or more of carbonate bonds, and frequently 95% or more of carbonate bonds. The polycarbonate prepared according to the present invention is a polymer which is easily decomposed and has neither residue nor soot upon combustion, and is thus useful in for example packaging materials, heat-insulating materials, or coating materials.

In addition, the present invention provides a method of preparing polycarbonate, comprising copolymerizing carbon dioxide and one or more epoxide compounds selected from the group consisting of (C2-C20)alkylene oxide substituted or unsubstituted with halogen, (C1-C20)alkyloxy, (C6-C20) aryloxy or (C6-C20)ar(C1-C20)alkyloxy; (C4-C20)cycloalkylene oxide substituted or unsubstituted with halogen, (C1-C20)alkyloxy, (C6-C20)aryloxy or (C6-C20)ar(C1-C20)alkyloxy; and (C8-C20)styrene oxide substituted or unsubstituted with halogen, (C1-C20)alkyloxy, (C6-C20) aryloxy, (C6-C20)ar(C1-C20)alkyloxy or (C1-C20)alkyl using a complex compound of Formula 3 below including the complex compound of Formula 1 as a catalyst, thus preparing polycarbonate; and bringing a solution in which the prepared copolymer and the catalyst are dissolved into contact with a solid inorganic material, a polymer material or a mixture thereof insoluble in the solution, thus forming a composite of solid inorganic material or polymer material and catalyst, thereby separating the copolymer and the catalyst from each other.

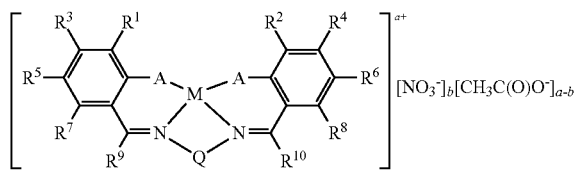

[Formula 3]

In Formula 3, M is trivalent cobalt or trivalent chromium;

A is oxygen or sulfur;

Q is a diradical that connects two nitrogen atoms;

$R^1$ to $R^{10}$ are each independently hydrogen; halogen; (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20) aryl (C1-C20) alkyl; (C6-C20) aryl (C1-C20)alkyl containing one or more selected from among halogen, nitrogen, oxygen, silicon, sulfur and phosphorus; (C1-C20)alkoxy; (C6-C30)aryloxy; formyl; (C1-C20)alkylcarbonyl; (C6-C20)arylcarbonyl; or a metalloid radical of Group 14 metal substituted with hydrocarbyl;

two of $R^1$ to $R^{10}$ may be linked with each other to form a ring;

at least one of $R^3$ to $R^{10}$ is a proton group selected from among Formula a, Formula b and Formula c as represented below:

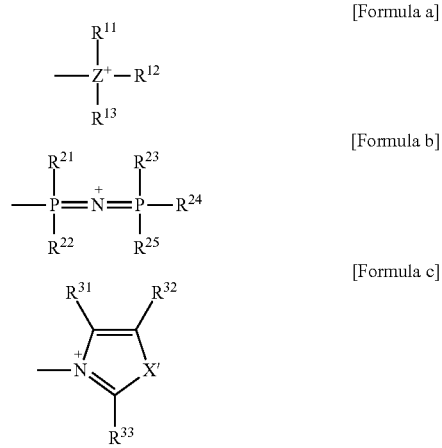

Z is nitrogen or phosphorus;

$R^{11}$, $R^{12}$, $R^{13}$, $R^{21}$, $R^{22}$, $R^{23}$, $R^{24}$ and $R^{25}$ are each independently (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; or a metalloid radical of Group 14 metal substituted with hydrocarbyl; two of $R^{11}$, $R^{12}$ and $R^{13}$ or two of $R^{21}$, $R^{22}$, $R^{23}$, $R^{24}$ and $R^{25}$ may be linked with each other to form a ring;

$R^{31}$, $R^{32}$ and $R^{33}$ are each independently hydrogen; (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; or a metalloid radical of Group 14 metal substituted with hydrocarbyl; two of $R^{31}$, $R^{32}$ and $R^{33}$ may be linked with each other to form a ring;

X' is oxygen, sulfur or N—R (wherein R is (C1-C20)alkyl);

a is a number obtained by adding 1 to the number of proton groups included in $R^3$ to $R^{10}$;

b is an integer of 1 or more; and a nitrate or acetate anion may be coordinated to M.

The mechanism of the method of removing a catalyst according to the present invention is the same as that known by the present inventors (Korean Patent Application No. 10-2008-0015454; Angew. Chem. Int. Ed., 2008, 47, 7306-7309. (2008.09.08)). However, a compound in which an anion is nitrate was not included in the known patent. Copolymerization of carbon dioxide/epoxide using an analogous compound having a nitrate anion is known in the Chinese Patent but the method of removing a catalyst is not mentioned (CN 100494248C (2009.06.03)). The present invention provides not only the copolymer prepared using the compound of Formula 1 and the method of separating the copolymer and the catalyst, but also the copolymer prepared using the compound of Formula 3, which may have slightly decreased polymerization activity because $R^1$ and $R^2$ are not necessarily primary alkyl and the number of onium salts is two or less, and also which may fall in a wider range, and the method of separating the copolymer and the catalyst.

The solid inorganic material may be silica or alumina which has been surface modified or not, and the polymer material may be a polymer material having a functional group able to cause deprotonation by an alkoxy anion, in which the functional group able to cause deprotonation by an alkoxy anion may include a sulfonic acid group, a carboxylic acid group, a phenol group, or an alcohol group.

Specific examples of the solid inorganic material composed mainly of silicon or aluminum having a Bronsted acid site which may act to supply a proton to an alkoxy anion or a carbonate anion include silica, alumina, aluminosilicate (zeolite), aluminophosphate, titanium silicate, and clay. Particularly useful is silica or alumina which has been surface modified or not.

The polymer material is preferably a material which is crosslinked with having a number average molecular weight of 500~10,000,000, and also may be used so long as it does not dissolve in a solution including a copolymer and a catalyst even when not crosslinked. Specific examples of the polymer material having a functional group able to cause deprotonation by an alkoxy anion include copolymers comprising polymer chains including monomers represented by Formulas A to E below, or homopolymers composed exclusively of such monomers. As the polymer material acting as such a support, any material which is not crosslinked may be used as long as it does not dissolve in the aforementioned solution. However, it is preferable that a polymer material which is appropriately crosslinked is used to decrease solubility.

[Formula A]

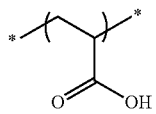

[Formula B]

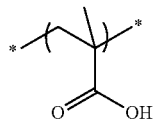

[Formula C]

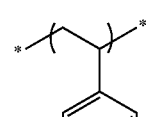

[Formula D]

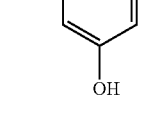

[Formula E]

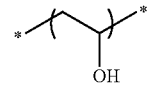

In addition, the present invention provides a method of separating and recovering a catalyst and a catalyst precursor from a solution in which a copolymer and the catalyst are dissolved, comprising copolymerizing carbon dioxide and one or more epoxide compounds selected from the group consisting of (C2-C20)alkylene oxide substituted or unsubstituted with halogen, (C1-C20)alkyloxy, (C6-C20)aryloxy or (C6-C20)ar(C1-C20)alkyloxy; (C4-C20)cycloalkylene oxide substituted or unsubstituted with halogen, (C1-C20) alkyloxy, (C6-C20)aryloxy or (C6-C20)ar(C1-C20)alkyloxy; and (C8-C20)styrene oxide substituted or unsubstituted with halogen, (C1-C20)alkyloxy, (C6-C20)aryloxy, (C6-C20)ar(C1-C20)alkyloxy or (C1-C20)alkyl using the complex compound of Formula 3 as a catalyst, thus preparing polycarbonate; bringing a solution in which the prepared copolymer and the catalyst are dissolved into contact with a solid inorganic material, a polymer material or a mixture thereof insoluble in the solution, thus forming a composite of solid inorganic material or polymer material and catalyst, thereby separating the copolymer and the catalyst from each other; and treating the composite of solid inorganic material or polymer material and catalyst with nitric acid or nitrate salt in a medium which does not dissolve the composite of solid inorganic material or polymer material and catalyst, thus dissolving out the catalyst or the catalyst precursor from the medium, thereby separating and recovering the catalyst and the catalyst precursor. Particularly useful as the medium is ethanol or methanol.

In the known method of recovering a catalyst, a non-reactive salt such as $NaBF_4$ is used (Korean Patent Application No. 10-2008-0015454; Angew. Chem. Int. Ed., 2008, 47, 7306-7309. (2008.09.08)), whereas nitric acid or nitrate salt which is comparatively very low-priced is used in the present invention.

In addition, the present invention provides a method of preparing a complex compound of Formula 1 below, comprising reacting a compound of Formula 4 below with silver nitrate ($AgNO_3$) or a mixture of silver nitrate ($AgNO_3$) and silver acetate ($AgOC(O)CH_3$) corresponding to an equivalent of a halogen anion contained in Formula 4, thus preparing a compound of Formula 5 below; and reacting the compound of Formula 5 with cobalt (II) acetate or chromium (II) acetate in the presence of oxygen, thus preparing the complex compound of Formula 1.

[Formula 1]

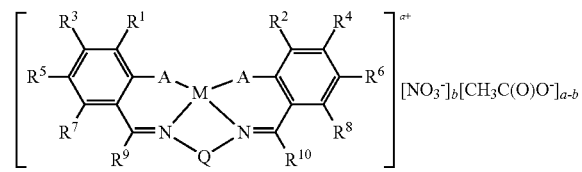

[Formula 4]

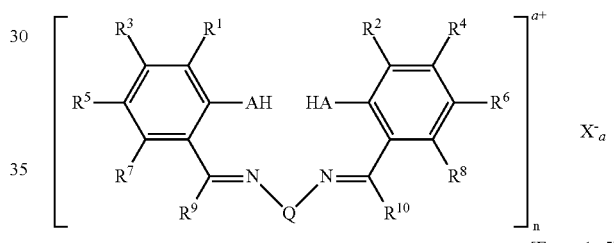

[Formula 5]

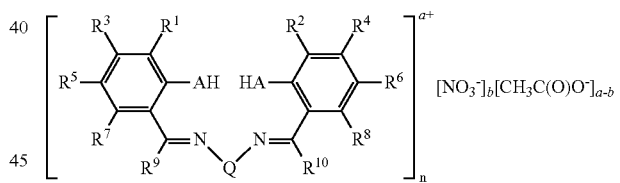

In Formulas 1, 4 and 5, M is trivalent cobalt or trivalent chromium;

A is an oxygen or sulfur atom;

Q is a diradical that connects two nitrogen atoms;

$X^-$ is a halogen anion;

$R^1$ and $R^2$ are each independently (C1-C20) primary alkyl;

$R^3$ to $R^{10}$ are each independently hydrogen; halogen; (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; (C1-C20)alkoxy; (C6-C30)aryloxy; formyl; (C1-C20) alkylcarbonyl; (C6-C20)arylcarbonyl; or a metalloid radical of Group 14 metal substituted with hydrocarbyl;

two of $R^1$ to $R^{10}$ may be linked with each other to form a ring;

at least three of $R^3$ to $R^{10}$ are a proton group selected from among Formula a, Formula b and Formula c as represented below:

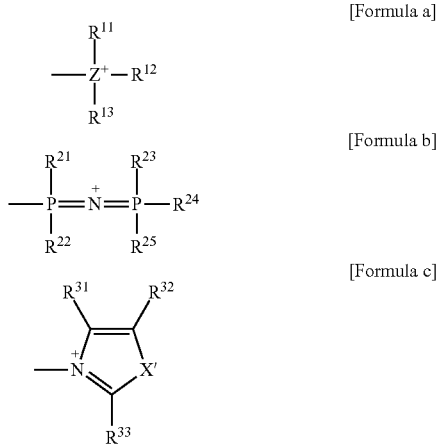

[Formula a]

[Formula b]

[Formula c]

Z is nitrogen or phosphorus;

$R^{11}, R^{12}, R^{13}, R^{21}, R^{22}, R^{23}, R^{24}$ and $R^{25}$ are each independently (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; or a metalloid radical of Group 14 metal substituted with hydrocarbyl; two of $R^{11}, R^{12}$ and $R^{13}$ or two of $R^{21}, R^{22}, R^{23}, R^{24}$ and $R^{25}$ may be linked with each other to form a ring;

$R^{31}, R^{32}$ and $R^{33}$ are each independently hydrogen; (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; or a metalloid radical of Group 14 metal substituted with hydrocarbyl; two of $R^{31}, R^{32}$ and $R^{33}$ may be linked with each other to form a ring;

X' is oxygen, sulfur or N—R (wherein R is (C1-C20)alkyl);

a is a number obtained by adding 1 to the number of proton groups included in $R^3$ to $R^{10}$;

b is an integer of 1 or more; and a nitrate or acetate anion may be coordinated to M.

Used in the synthesis of the catalyst according to the present invention, $AgNO_3$ or Ag(OAc) is very inexpensive compared to $AgBF_4$, and also may be mass produced and purchased, and also eliminates the step of using ethanol without oxygen, and also obviates the need for NaH and anhydrous THF because of not using sodium 2,4-dinitrophenolate.

Preferably in Formulas 1, 4 and 5, M is trivalent cobalt; A is oxygen; Q is trans-1,2-cyclohexylene, phenylene or ethylene; $R^1$ and $R^2$ are each independently methyl or ethyl; $R^3$ to $R^{10}$ are each independently hydrogen or —[$YR^{41}_{3-m}\{(CR^{42}R^{43})_nN^+R^{44}R^{45}R^{46}\}_m$] in which Y is C or Si; $R^{41}, R^{42}, R^{43}, R^{44}, R^{45}$ and $R^{46}$ are each independently hydrogen; (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; or a metalloid radical of Group 14 metal substituted with hydrocarbyl, two of $R^{44}, R^{45}$ and $R^{46}$ being linked with each other to form a ring; m is an integer from 1 to 3, and n is an integer from 1 to 20, in which at least three of $R^3$ to $R^{10}$ are —[$YR^{41}_{3-m}\{(CR^{42}R^{43})_nN^+R^{44}R^{45}R^{46}\}_m$] when m is 1, at least two of $R^3$ to $R^{10}$ are —[$YR^{41}_{3-m}\{(CR^{42}R^{43})_nN^+R^{44}R^{45}R^{46}\}_m$] when m is 2, or one or more of $R^3$ to $R^{10}$ are —[$YR^{41}_{3-m}\{(CR^{42}R^{43})_nN^+R^{44}R^{45}R^{46}\}_m$] when m is 3.

More preferably, a method of preparing a compound of Formula 2 below is provided, which includes reacting a compound of Formula 6 below with four equivalents of silver nitrate ($AgNO_3$) thus preparing a compound of Formula 7 below; and reacting the compound of Formula 7 with cobalt (II) acetate in the presence of oxygen, thus preparing the compound of Formula 2.

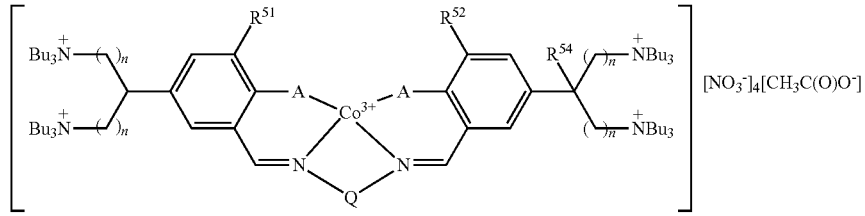

[Formula 2]

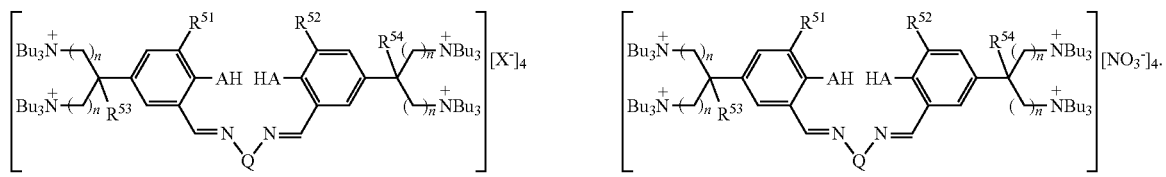

[Formula 6]    [Formula 7]

In Formulas 2, 6 and 7, $X^-$ is a halogen anion,
$R^{51}$ and $R^{52}$ are each independently methyl or ethyl;
$R^{53}$ and $R^{54}$ are each independently hydrogen or methyl;
Q is trans-1,2-cyclohexylene, phenylene or ethylene;
n is an integer from 1 to 20; and
a nitrate anion and an acetate anion may be coordinated to cobalt.

More preferably in Formulas 2, 6 and 7, $R^{51}$, $R^{52}$, $R^{53}$ and $R^{54}$ are methyl, n is 3, and Q is trans-1,2-cyclohexylene.

The synthesis of compounds of Formulas 6 and 7 is known in the paper and patent known by the present inventors (Korean Patent No. 10-0853358 (issue date: 2008.08.13); *Angew. Chem. Int. Ed.*, 2008, 47, 7306-7309; *Bull. Korean Chem. Soc.* 2009, 30, 745-748).

A better understanding of the present invention may be obtained thanks to the following examples which are set forth to illustrate, but are not to be construed to limit the present invention.

EXAMPLE 1

Synthesis of Catalyst (Compound C)

A method of simply and economically synthesizing a catalyst according to the present invention is shown below. Compound A was synthesized using a known method (*Bull. Korean Chem. Soc.* 2009, 30, 745-748).

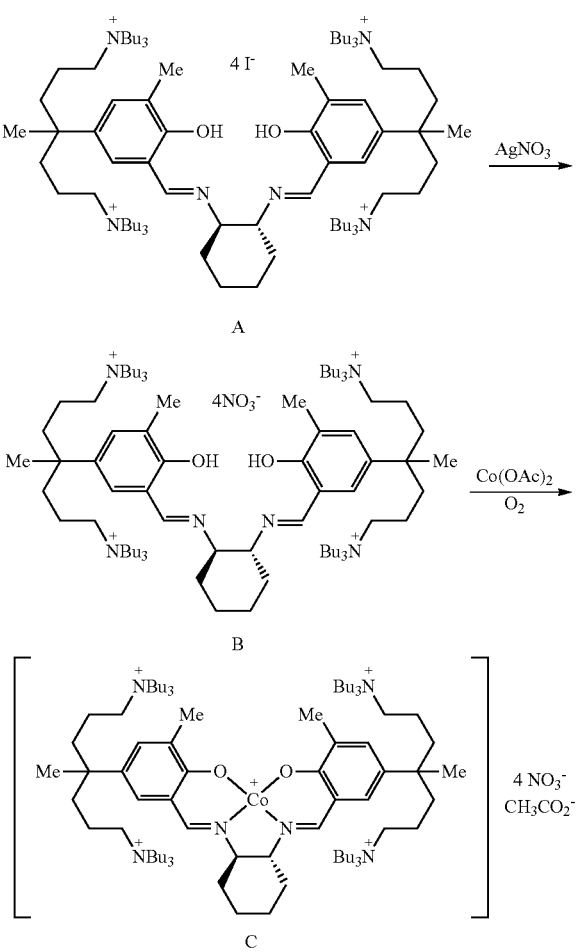

Synthesis of Compound B

Compound A (100 mg, 0.054 mmol) and $AgNO_3$ (37.3 mg, 0.219 mmol) were dissolved in ethanol (3 mL) and then stirred overnight. The stirred solution was filtered using celite and the produced AgI was removed. The solvent was removed under reduced pressure to yield the product, Compound B as a yellow solid powder (0.80 g, 94%).

$^1$H NMR ($CDCl_3$): δ 13.51 (s, 2H, OH), 8.48 (s, 2H, CH=N), 7.15 (s, 4H, m-H), 3.44 (br, 2H, cyclohexyl-CH), 3.19 (br, 32H, $NCH_2$), 2.24 (s, 6H, $CH_3$), 1.57-1.52 (br, 4H, cyclohexyl-$CH_2$), 1.43-1.26 (br, 74H), 0.90-0.70 (br, 36H, $CH_3$) ppm.

Synthesis of Compound C

Compound B (95 mg, 0.061 mmol) and $Co(OAc)_2$ (10.7 mg, 0.061 mmol) were placed in a flask, and added methylene chloride (3 mL) as a solvent. The resulting solution was stirred at room temperature for 3 hours under oxygen atmosphere. The solvent was removed under reduced pressure to yield the product, Compound C as a brown solid powder (85 mg, 83%).

$^1$H NMR (DMSO-$d_6$, 38° C.): major signal set, δ 7.83 (s, 2H, CH=N) 7.27 (br s, 2H, m-H), 7.22, 7.19 (br s, 2H, m-H), 3.88 (br, 1H, cyclohexyl-CH), 3.55 (br, 1H, cyclohexyl-CH), 3.30-2.90 (br, 32H, $NCH_2$), 2.58 (s, 3H, $CH_3$), 2.55 (s, 3H, $CH_3$), 2.10-1.80 (br, 4H, cyclohexyl-$CH_2$), 1.70-1.15 (br m, 74H), 1.0-0.80 (br, 36H, $CH_3$) ppm; minor signal set, δ 7.65 (s, 2H, CH=N) 7.45 (s, 2H, m-H), 7.35 (s, 2H, m-H), 3.60 (br, 2H, cyclohexyl-CH), 3.30-2.90 (br, 32H, $NCH_2$), 2.66 (s, 6H, $CH_3$), 2.10-1.80 (br, 4H, cyclohexyl-$CH_2$), 1.70-1.15 (br m, 74H), 1.0-0.80 (br, 36H, $CH_3$) ppm.

$^1$H NMR ($CD_2Cl_2$): δ 7.65 (br, 2H, CH=N) 7.34 (br, 2H, m-H), 7.16 (br, 2H, m-H), 3.40-2.00 (br, 32H, $NCH_2$), 2.93 (br s, 6H, $CH_3$), 2.10-1.80 (br m, 4H, cyclohexyl-$CH_2$), 1.70-1.15 (br m, 74H), 1.1-0.80 (br, 36H, $CH_3$) ppm.

In the $^1$H NMR spectrum obtained by dissolving Compound C in DMSO-$d_6$, two sets of signals were observed at a ratio of 6:4. The major signal set shows that two phenoxy ligands of the Salen unit are different, and the minor signal set shows that two phenoxy ligands are identical. This is considered that Compound C is in an equilibrium state as will be described below in a DMSO solvent. It has been proven that the case where a substituent having small steric hindrance such as methyl is located at an ortho-position of two phenoxy ligands of the Salen unit results in a structure in which the nitrogen of an imine is not coordinated in a polar solvent such as DMSO (*Inorg. Chem.* 2009, 48, 10455-10465). A single set of signals which is very broad was observed in methylene chloride which is a nonpolar solvent. Taking into consideration the weak coordination ability of the $NO_3^-$ anion, the following structure in which the nitrogen of an imine is coordinated and nitrate anions and acetate anion are coordinated and decoordinated while being exchanged on two axial coordination planes is expected.

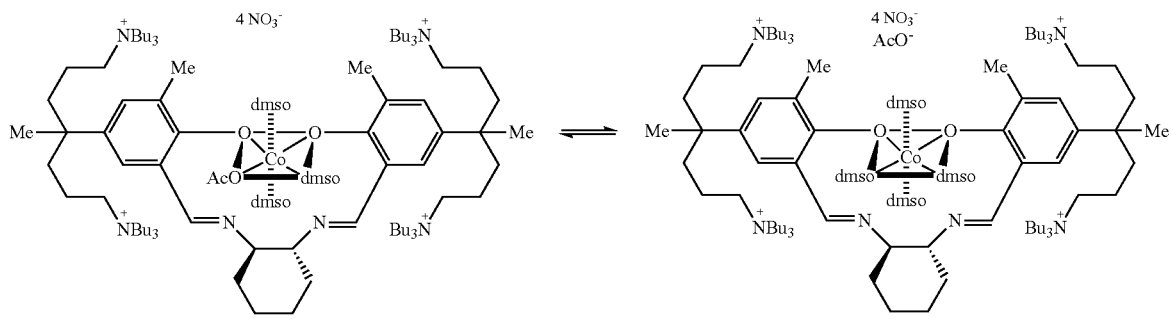

<Expected Structure of Compound C in DMSO>

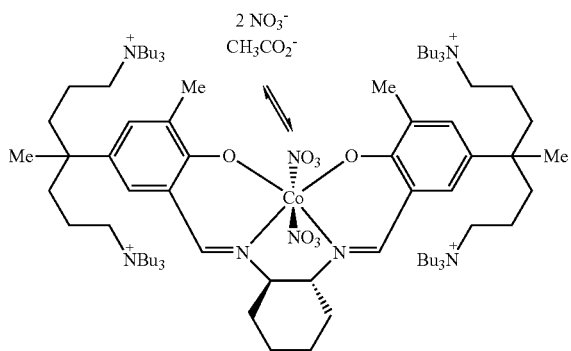

<Expected Structure of Compound C in CH$_2$Cl$_2$>

EXAMPLE 2

Carbon Dioxide/Propylene Oxide Copolymerization

Compound C (3.0 mg, monomer/catalyst=100,000) prepared in Example 1 and propylene oxide (10.0 g, 172 mmol) were added into a 50 mL bomb reactor, after which the reactor was assembled. A carbon dioxide pressure of 15 bar was applied to the reactor, the reactor was dipped in an oil bath at 73° C., and stirred. After 35 min, the internal temperature of the reactor reached 70° C. and the pressure of the reactor was observed to decrease. The polymerization was carried out for 1 hour. The reactor was dipped in a cooling bath and thus cooled, after which carbon dioxide gas was removed, and the reaction was terminated, resulting in a light yellow viscous solution.

EXAMPLE 3

Catalyst Separation

To the viscous solution prepared in Example 2 was further added 10 g of propylene oxide in order to reduce the viscosity of the solution, after which the solution was passed through a silica gel (400 mg, manufactured by Merck, 0.040~0.063 mm particle size (230~400 mesh)) column, yielding a colorless solution. The monomer was removed using vacuum decompression, thus obtaining 2.4 g of a colorless solid. This yield corresponds to TON (Turnover Number) of 15000, and TOF (Turnover Frequency) of 15000 h$^{-1}$. The polymer thus obtained had a molecular weight (M$_n$) of 217000 as measured using GPC and a molecular weight distribution (M$_w$/M$_n$) of 1.34. The selectivity for forming a polymer analyzed by $^1$H NMR was 99% or more.

EXAMPLE 4

Recovery of Catalyst Precursor

A reddish brown colored cobalt compound was extracted from a silica column having the catalyst of Example 3 using a NaNO$_3$-saturated methanol solution as an elution solution. The yellow compound was completely extracted, and the color of the silica column was white which is an inherent color of silica. Methanol was removed from the extract using vacuum distillation. The residue was dissolved in dichloromethane (3 mL) and filtered, so that excess NaNO$_3$ was removed. The filtrate was added with 1 mL of 2 N HNO$_3$ aqueous solution and stirred at 85° C. overnight. The aqueous solution layer was removed and the organic layer was washed with 1 mL of water. The organic layer was dried with anhydrous MgSO$_4$ and the solvent was removed under reduced pressure. Silica gel column chromatography using a mixture solvent of ethanol and methylene chloride at 10:1 was performed, thus obtaining the following aldehyde compound. The recovery rate was 90%. The catalyst can be easily prepared from this aldehyde compound.

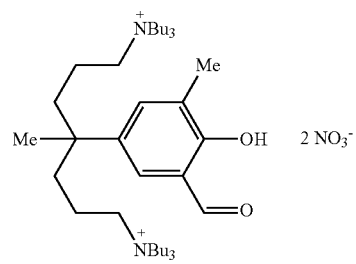

<Recovered Catalyst Precursor>

As described hereinbefore, the present invention provides a catalytic system of nitrate anions for carbon dioxide/epoxide copolymerization. Conventional synthesis methods use explosive 2,4-dinitrophenolate or 2,4-dinitrophenol, and upon carbon dioxide/epoxide copolymerization using a catalyst including the same, the 2,4-dinitrophenol group is attached to the end of the polymer chain, and thus 2,4-dinitrophenolate and 2,4-dinitrophenol are not recovered in the step of recovering the catalyst. Thereby, the price of resin becomes increased and the color of resin may change. Furthermore, upon preparation of the catalyst, high-priced AgBF$_4$ is used, a solvent such as oxygen-free ethanol and anhydrous THF is used, undesirably complicating the preparation of the catalyst, and NaH having high ignitability is used. Also, upon recovery of the catalyst, high-priced NaBF$_4$ is used, thus negating economic benefits.

According to the present invention, a method of preparing a complex compound having a novel structure is advantageous because nitrate anions and acetate anions are used instead of explosive 2,4-dinitrophenolate, thus enabling mass production of the catalyst, and also because a nitrate group or an acetate group is attached to the end of the polymer chain and thus the catalyst cost is low upon mass production. Furthermore, upon preparation of the catalyst, in lieu of expensive AgBF$_4$, AgNO$_3$ which is inexpensive and may be mass produced and purchased is used, resulting in low catalyst preparation cost. Also, because of not using a solvent such as oxygen-free ethanol and anhydrous THF, the catalyst can be simply prepared, and NaH having high ignitability is not used. Moreover, nitric acid or nitrate is used for catalyst recovery, in place of expensive NaBF$_4$, thus generating economic benefits.

Also, after carbon dioxide/epoxide copolymerization using the complex compound according to the present invention as a catalyst, the used catalyst can be separated, recovered and re-used, thus reducing the catalyst cost, thereby economically preparing a copolymer. Because the catalyst which is a metal compound can be removed from the copolymer, it is possible to prepare a highly pure copolymer, consequently widening the application range of copolymer and enhancing the durability and processability of the polymer.

Although the embodiments of the present invention have been disclosed for illustrative purposes, those skilled in the art will appreciate that a variety of different modifications, additions and substitutions are possible, without departing from the scope and spirit of the invention as disclosed in the accompanying claims. Accordingly, such modifications, additions and substitutions should also be understood as falling within the scope of the present invention.

What is claimed is:

1. A complex compound represented by Formula 1 below:

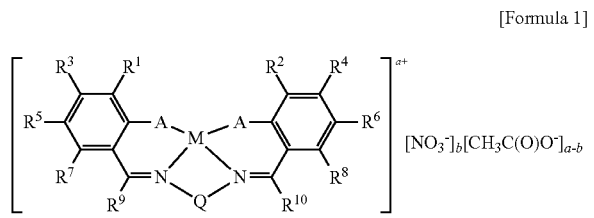

[Formula 1]

In Formula 1, M is trivalent cobalt or trivalent chromium;
A is an oxygen or sulfur atom;
Q is a diradical that connects two nitrogen atoms;
$R^1$ and $R^2$ are each independently (C1-C20) primary alkyl;
$R^3$ to $R^{10}$ are each independently hydrogen; halogen; (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halo- gen, nitrogen, oxygen, silicon, sulfur and phosphorus; (C1-C20)alkoxy; (C6-C30)aryloxy; formyl; (C1-C20)alkylcarbonyl; (C6-C20)arylcarbonyl; or a metalloid radical of Group 14 metal substituted with hydrocarbyl;
two of $R^1$ to $R^{10}$ may be linked with each other to form a ring;
at least three of $R^3$ to $R^{10}$ are a proton group selected from among Formula a, Formula b and Formula c as represented below:

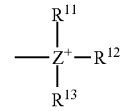

[Formula a]

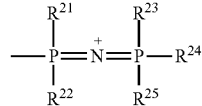

[Formula b]

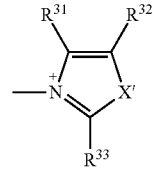

[Formula c]

Z is nitrogen or phosphorus;
$R^{11}$, $R^{12}$, $R^{13}$, $R^{21}$, $R^{22}$, $R^{23}$, $R^{24}$ and $R^{25}$ are each independently (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; or a metalloid radical of Group 14 metal substituted with hydrocarbyl; two of $R^{11}$, $R^{12}$ and $R^{13}$ or two of $R^{21}$, $R^{22}$, $R^{23}$, $R^{24}$ and $R^{25}$ may be linked with each other to form a ring;
$R^{31}$, $R^{32}$ and $R^{33}$ are each independently hydrogen; (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; or a metalloid radical of Group 14 metal substituted with hydrocarbyl; two of $R^{31}$, $R^{32}$ and $R^{33}$ may be linked with each other to form a ring;
X' is oxygen, sulfur or N—R (wherein R is (C1-C20)alkyl);
a is a number obtained by adding 1 to the number of proton groups included in $R^3$ to $R^{10}$;
b is an integer of 1 or more; and
a nitrate or acetate anion may be coordinated to M.

2. The complex compound of claim 1, wherein Q is (C6-C30)arylene, (C1-C20)alkylene, (C2-C20)alkenylene, (C2-C20)alkynylene, or (C3-C20)cycloalkylene.

3. The complex compound of claim 2, wherein M is trivalent cobalt;
A is oxygen;
Q is trans-1,2-cyclohexylene, phenylene or ethylene;
$R^1$ and $R^2$ are each independently methyl or ethyl;
$R^3$ to $R^{10}$ are each independently hydrogen or —[$YR^{41}_{3-m}\{(CR^{42}R^{43})_nN^+R^{44}R^{45}R^{46}\}_m$];
Y is C or Si;
$R^{41}$, $R^{42}$, $R^{43}$, $R^{44}$, $R^{45}$ and $R^{46}$ are each independently hydrogen; (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; or a metalloid radical of Group 14 metal substituted with hydrocarbyl, two of $R^{44}$, $R^{45}$ and $R^{46}$ being linked with each other to form a ring;
m is an integer from 1 to 3, and n is an integer from 1 to 20, in which at least three of $R^3$ to $R^{10}$ are —[$YR^{41}_{3-m}\{(CR^{42}R^{43})_nN^+R^{44}R^{45}R^{46}\}_m$] when m is 1, at least two of $R^3$ to $R^{10}$ are —[$YR^{41}_{3-m}\{(CR^{42}R^{43})_nN^+R^{44}R^{45}R^{46}\}_m$] when m is 2, or one or more of $R^3$ to $R^{10}$ are —[$YR^{41}_{3-m}\{(CR^{42}R^{43})_nN^+R^{44}R^{45}R^{46}\}_m$] when m is 3.

4. The complex compound of claim 3, which is a complex compound represented by Formula 2 below:

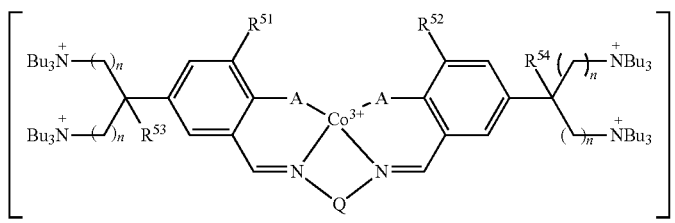

[Formula 2]

$[NO_3^-]_4[CH_3C(O)O^-]$

In Formula 2, $R^{51}$ and $R^{52}$ are each independently methyl or ethyl;
$R^{53}$ and $R^{54}$ are each independently hydrogen or methyl;
Q is trans-1,2-cyclohexylene, phenylene or ethylene;
n is an integer from 1 to 20; and
a nitrate anion and an acetate anion may be coordinated to cobalt.

5. The complex compound of claim 4, wherein $R^{51}$, $R^{52}$, $R^{53}$ and $R^{54}$ are methyl, n is 3, and Q is trans-1,2-cyclohexylene.

6. A method of preparing polycarbonate, comprising copolymerizing an epoxide compound and carbon dioxide using the complex compound of claim 1 as a catalyst.

7. The method of claim 6, wherein the epoxide compound is one or more selected from the group consisting of (C2-C20)alkylene oxide substituted or unsubstituted with halogen, (C1-C20)alkyloxy, (C6-C20)aryloxy or (C6-C20)ar(C1-C20)alkyloxy; (C4-C20)cycloalkylene oxide substituted or unsubstituted with halogen, (C1-C20)alkyloxy, (C6-C20)aryloxy or (C6-C20)ar(C1-C20)alkyloxy; and (C8-C20)styrene oxide substituted or unsubstituted with halogen, (C1-C20)alkyloxy, (C6-C20)aryloxy, (C6-C20)ar(C1-C20)alkyloxy or (C1-C20)alkyl.

8. A method of preparing polycarbonate, comprising:
copolymerizing carbon dioxide and one or more epoxide compounds selected from the group consisting of (C2-C20)alkylene oxide substituted or unsubstituted with halogen, (C1-C20)alkyloxy, (C6-C20)aryloxy or (C6-C20)ar(C1-C20)alkyloxy; (C4-C20)cycloalkylene oxide substituted or unsubstituted with halogen, (C1-C20)alkyloxy, (C6-C20)aryloxy or (C6-C20)ar(C1-C20)alkyloxy; and (C8-C20)styrene oxide substituted or unsubstituted with halogen, (C1-C20)alkyloxy, (C6-C20)aryloxy, (C6-C20)ar(C1-C20)alkyloxy or (C1-C20)alkyl using a complex compound of Formula 3 below as a catalyst, thus preparing polycarbonate; and
bringing a solution in which the prepared copolymer and the catalyst are dissolved into contact with a solid inorganic material, a polymer material or a mixture thereof insoluble in the solution, thus forming a composite of solid inorganic material or polymer material and catalyst, thereby separating the copolymer and the catalyst from each other:

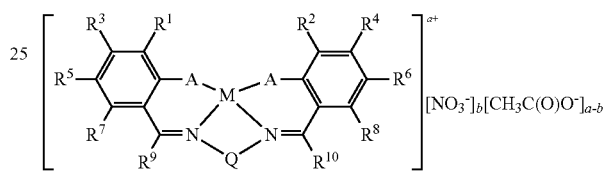

[Formula 3]

$[NO_3^-]_b[CH_3C(O)O^-]_{a-b}$

In Formula 3, M is trivalent cobalt or trivalent chromium;
A is oxygen or sulfur;
Q is a diradical that connects two nitrogen atoms;
$R^1$ to $R^{10}$ are each independently hydrogen; halogen; (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; (C1-C20)alkoxy; (C6-C30)aryloxy; formyl; (C1-C20)alkylcarbonyl; (C6-C20)arylcarbonyl; or a metalloid radical of Group 14 metal substituted with hydrocarbyl;
two of $R^1$ to $R^{10}$ may be linked with each other to form a ring;
at least one of $R^3$ to $R^{10}$ is a proton group selected from among Formula a, Formula b and Formula c as represented below:

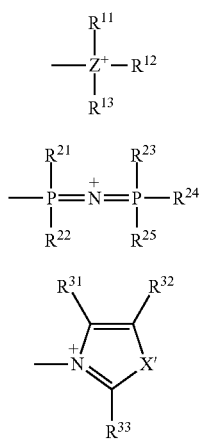

[Formula a]

[Formula b]

[Formula c]

Z is nitrogen or phosphorus;

$R^{11}$, $R^{12}$, $R^{13}$, $R^{21}$, $R^{22}$, $R^{23}$, $R^{24}$ and $R^{25}$ are each independently (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; or a metalloid radical of Group 14 metal substituted with hydrocarbyl; two of $R^{11}$, $R^{12}$ and $R^{13}$ or two of $R^{21}$, $R^{22}$, $R^{23}$, $R^{24}$ and $R^{25}$ may be linked with each other to form a ring;

$R^{31}$, $R^{32}$ and $R^{33}$ are each independently hydrogen; (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; or a metalloid radical of Group 14 metal substituted with hydrocarbyl; two of $R^{31}$, $R^{32}$ and $R^{33}$ may be linked with each other to form a ring;

X' is oxygen, sulfur or N—R (wherein R is (C1-C20)alkyl);

a is a number obtained by adding 1 to the number of proton groups included in $R^3$ to $R^{10}$;

b is an integer of 1 or more; and a nitrate or acetate anion may be coordinated to M.

9. The method of claim 8, wherein the solid inorganic material is a silica or alumina which has been surface modified or not, and the solid polymer material is a polymer material having a functional group able to cause deprotonation by an alkoxy anion.

10. The method of claim 9, wherein the functional group able to cause deprotonation by an alkoxy anion is a sulfonic acid group, a carboxylic acid group, a phenol group or an alcohol group.

11. A method of separating and recovering a catalyst and a catalyst precursor from a solution in which a copolymer and the catalyst are dissolved, comprising:

copolymerizing carbon dioxide and one or more epoxide compounds selected from the group consisting of (C2-C20)alkylene oxide substituted or unsubstituted with halogen or (C1-C20)alkoxy; (C4-C20)cycloalkylene oxide substituted or unsubstituted with halogen or (C1-C20)alkoxy; and (C8-C20)styrene oxide substituted or unsubstituted with halogen, (C1-C20)alkoxy or (C1-C20)alkyl using a complex compound of Formula 3 below as a catalyst, thus preparing polycarbonate;

bringing a solution in which the prepared copolymer and the catalyst are dissolved into contact with a solid inorganic material, a polymer material or a mixture thereof insoluble in the solution, thus forming a composite of solid inorganic material or polymer material and catalyst, thereby separating the copolymer and the catalyst from each other; and treating the composite of solid inorganic material or polymer material and catalyst with nitric acid or nitrate salt in a medium which does not dissolve the composite of solid inorganic material or polymer material and catalyst, thus dissolving out the catalyst or the catalyst precursor from the medium, thereby separating and recovering the catalyst and the catalyst precursor:

[Formula 3]

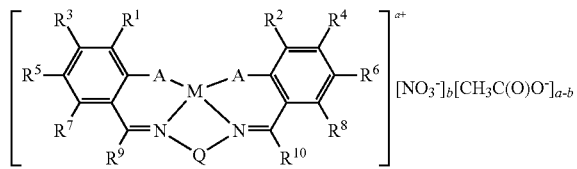

In Formula 3, M is trivalent cobalt or trivalent chromium;

A is oxygen or sulfur;

Q is a diradical that connects two nitrogen atoms;

$R^1$ to $R^{10}$ are each independently hydrogen; halogen; (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; (C1-C20)alkoxy; (C6-C30)aryloxy; formyl; (C1-C20)alkylcarbonyl; (C6-C20)arylcarbonyl; or a metalloid radical of Group 14 metal substituted with hydrocarbyl;

two of $R^1$ to $R^{10}$ may be linked with each other to form a ring;

at least one of $R^3$ to $R^{10}$ is a proton group selected from among Formula a, Formula b and Formula c as represented below:

[Formula a]

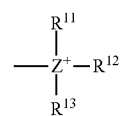

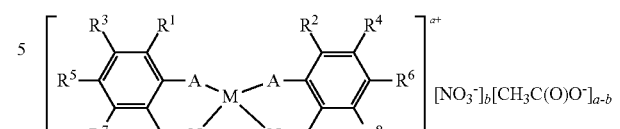

[Formula 1]

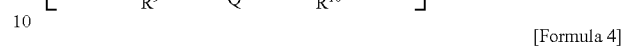

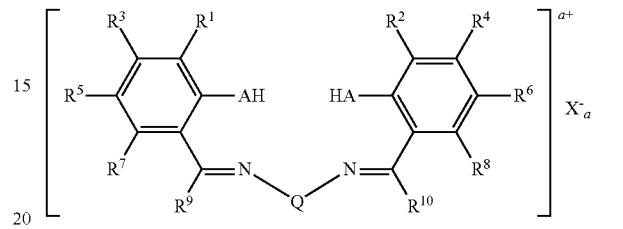

[Formula 4]

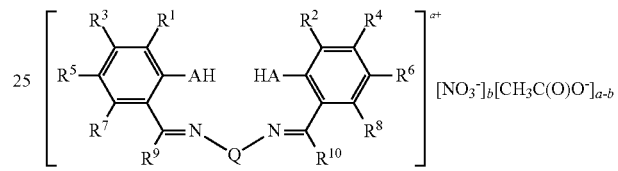

[Formula 5]

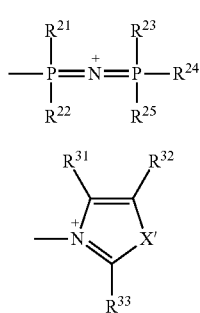

[Formula b]

[Formula c]

Z is nitrogen or phosphorus;

$R^{11}, R^{12}, R^{13}, R^{21}, R^{22}, R^{23}, R^{24}$ and $R^{25}$ are each independently (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; or a metalloid radical of Group 14 metal substituted with hydrocarbyl; two of $R^{11}, R^{12}$ and $R^{13}$ or two of $R^{21}, R^{22}, R^{23}, R^{24}$ and $R^{25}$ may be linked with each other to form a ring;

$R^{31}, R^{32}$ and $R^{33}$ are each independently hydrogen; (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; or a metalloid radical of Group 14 metal substituted with hydrocarbyl; two of $R^{31}, R^{32}$ and $R^{33}$ may be linked with each other to form a ring;

X' is oxygen, sulfur or N—R (wherein R is (C1-C20)alkyl);

a is a number obtained by adding 1 to the number of proton groups included in $R^3$ to $R^{10}$;

b is an integer of 1 or more; and a nitrate or acetate anion may be coordinated to M.

12. A method of preparing the complex compound of Formula 1 of claim 1, comprising:

reacting a compound of Formula 4 below with silver nitrate (AgNO$_3$) or a mixture of silver nitrate (AgNO$_3$) and silver acetate (AgOC(O)CH$_3$) corresponding to an equivalent of a halogen anion contained in Formula 4, thus preparing a compound of Formula 5 below; and reacting the compound of Formula 5 with cobalt (II) acetate or chromium (II) acetate in presence of oxygen, thus preparing the complex compound of Formula 1 below:

In Formulas 1, 4 and 5, M is trivalent cobalt or trivalent chromium;

A is an oxygen or sulfur atom;

Q is a diradical that connects two nitrogen atoms;

X⁻ is a halogen anion;

$R^1$ and $R^2$ are each independently (C1-C20) primary alkyl;

$R^3$ to $R^{10}$ are each independently hydrogen; halogen; (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; (C1-C20)alkoxy; (C6-C30)aryloxy; formyl; (C1-C20)alkylcarbonyl; (C6-C20)arylcarbonyl; or a metalloid radical of Group 14 metal substituted with hydrocarbyl;

two of $R^1$ to $R^{10}$ may be linked with each other to form a ring;

at least three of $R^3$ to $R^{10}$ are a proton group selected from among Formula a, Formula b and Formula c as represented below:

[Formula a]

[Formula b]

$$\begin{array}{c} R^{21} \quad R^{23} \\ | \quad | \\ \text{---}P\overset{+}{=}N\text{=}P\text{---}R^{24} \\ | \quad | \\ R^{22} \quad R^{25} \end{array}$$

[Formula c]

$$\begin{array}{c} R^{31} \quad R^{32} \\ \diagdown \quad \diagup \\ \text{---}\overset{+}{N} \quad X' \\ \diagdown \quad \diagup \\ R^{33} \end{array}$$

Z is nitrogen or phosphorus;

$R^{11}$, $R^{12}$, $R^{13}$, $R^{21}$, $R^{22}$, $R^{23}$, $R^{24}$ and $R^{25}$ are each independently (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; or a metalloid radical of Group 14 metal substituted with hydrocarbyl; two of $R^{11}$, $R^{12}$ and $R^{13}$ or two of $R^{21}$, $R^{22}$, $R^{23}$, $R^{24}$ and $R^{25}$ may be linked with each other to form a ring;

$R^{31}$, $R^{32}$ and $R^{33}$ are each independently hydrogen; (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; or a metalloid radical of Group 14 metal substituted with hydrocarbyl; two of $R^{31}$, $R^{32}$ and $R^{33}$ may be linked with each other to form a ring;

X' is oxygen, sulfur or N—R (wherein R is (C1-C20)alkyl);

a is a number obtained by adding 1 to the number of proton groups included in $R^3$ to $R^{10}$;

b is an integer of 1 or more; and a nitrate or acetate anion may be coordinated to M.

13. The method of claim 12, wherein M is trivalent cobalt;

A is oxygen;

Q is trans-1,2-cyclohexylene, phenylene or ethylene;

$R^1$ and $R^2$ are each independently methyl or ethyl;

$R^3$ to $R^{10}$ are each independently hydrogen or —[$YR^{41}_{3-m}\{(CR^{42}R^{43})_n N^+ R^{44}R^{45}R^{46}\}_m$];

Y is C or Si;

$R^{41}$, $R^{42}$, $R^{43}$, $R^{44}$, $R^{45}$ and $R^{46}$ are each independently hydrogen; (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; or a metalloid radical of Group 14 metal substituted with hydrocarbyl, two of $R^{44}$, $R^{45}$ and $R^{46}$ being linked with each other to form a ring;

m is an integer from 1 to 3, and n is an integer from 1 to 20, in which at least three of $R^3$ to $R^{10}$ are —[$YR^{41}_{3-m}\{(CR^{42}R^{43})_n N^+ R^{44}R^{45}R^{46}\}_m$] when m is 1, at least two of $R^3$ to $R^{10}$ are —[$YR^{41}_{3-m}\{(CR^{42}R^{43})_n N^+ R^{44}R^{45}R^{46}\}_m$] when m is 2, or one or more of $R^3$ to $R^{10}$ are —[$YR^{41}_{3-m}\{(CR^{42}R^{43})_n N^+ R^{44}R^{45}R^{46}\}_m$] when m is 3.

14. The method of claim 13, comprising:

reacting a compound of Formula 6 below with four equivalents of silver nitrate ($AgNO_3$), thus preparing a compound of Formula 7 below; and reacting the compound of Formula 7 with cobalt (II) acetate in the presence of oxygen, thus preparing a compound of Formula 2 below:

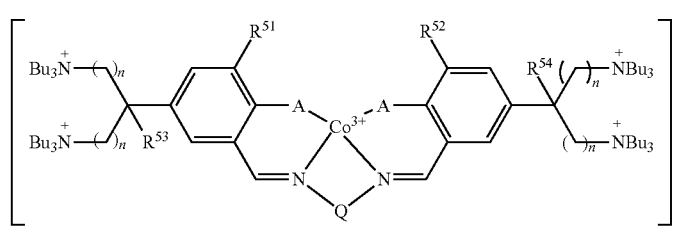

[Formula 2]

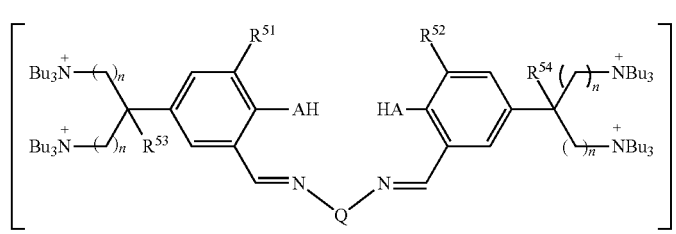

[Formula 6]

-continued

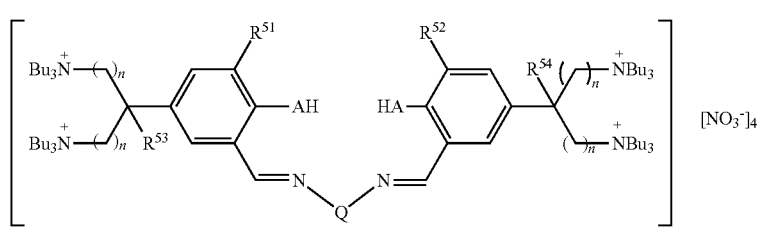

[Formula 7]

In Formulas 2, 6 and 7, X⁻ is a halogen anion,
$R^{51}$ and $R^{52}$ are each independently methyl or ethyl;
$R^{53}$ and $R^{54}$ are each independently hydrogen or methyl;
Q is trans-1,2-cyclohexylene, phenylene or ethylene;
n is an integer from 1 to 20; and
a nitrate anion and an acetate anion may be coordinated to cobalt.

15. The method of claim 14, wherein $R^{51}$, $R^{52}$, $R^{53}$ and $R^{54}$ are methyl, n is 3, and Q is trans-1,2-cyclohexylene.

* * * * *